(12) United States Patent
Cantatore

(10) Patent No.: US 8,712,516 B2
(45) Date of Patent: Apr. 29, 2014

(54) BIOMEDICAL ELECTRO-STIMULATOR

(75) Inventor: Eugenio Cantatore, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 143 days.

(21) Appl. No.: 12/682,802

(22) PCT Filed: Oct. 14, 2008

(86) PCT No.: PCT/IB2008/054221
§ 371 (c)(1),
(2), (4) Date: Apr. 13, 2010

(87) PCT Pub. No.: WO2009/050647
PCT Pub. Date: Apr. 23, 2009

(65) Prior Publication Data
US 2010/0211145 A1     Aug. 19, 2010

(30) Foreign Application Priority Data

Oct. 18, 2007   (EP) .................................... 07118776

(51) Int. Cl.
*A61N 1/00* (2006.01)
(52) U.S. Cl.
USPC .......................................................... 607/2
(58) Field of Classification Search
USPC ....................................................... 607/2, 5
See application file for complete search history.

(56) References Cited

U.S. PATENT DOCUMENTS

| | | | | |
|---|---|---|---|---|
| 5,447,522 | A | * | 9/1995 | Chang et al. ...................... 607/7 |
| 5,769,877 | A | * | 6/1998 | Barreras, Sr. .................... 607/61 |
| 6,018,227 | A | | 1/2000 | Kumar et al. |

(Continued)

FOREIGN PATENT DOCUMENTS

| | | |
|---|---|---|
| EP | 1610437 A1 | 12/2005 |
| EP | 1862196 A2 | 12/2007 |
| WO | 0069012 A1 | 11/2000 |
| WO | 2006123905 A1 | 11/2006 |

OTHER PUBLICATIONS

O'Loughlin et al: "Energy Trapping and Adaptive Clocking Innovations Applied to Capacitor Charging Series Resonant Inverters"; Conference Record of the Twenty-Fifth International Power Modulator Symposium, 2002 AMD 2002 High-Voltage Workshop, 2002, pp. 137-137.

(Continued)

*Primary Examiner* — Christopher D Koharski
*Assistant Examiner* — Philip Edwards

(57) ABSTRACT

A power efficient biomedical electro-stimulator circuit BSC is provided. The circuit BSC includes a charging circuit arranged to control charging of a storage capacitor C based on electric energy from an energy source ES, e.g. a battery. The charging circuit includes an energy converter EC that applies a charging current I to the storage capacitor C, this charging current I being substantially constant over a charging period T, thereby providing a power efficient charging. In preferred embodiments, the energy converter EC is an inductive energy converter, e.g. a DC-DC converter, with a control circuit serving to provide an almost constant charging current during the charging period. In another embodiment, the energy converter EC is an energy converter that charges the storage capacitor via a series resonator, e.g. a series connection of an inductor and a capacitor. The proposed biomedical electro-stimulator circuit is advantageous for devices such as pacemakers, and neural stimulation etc. which can benefit of increased battery lifetime due to an efficient charging scheme.

10 Claims, 3 Drawing Sheets

(56) References Cited

U.S. PATENT DOCUMENTS

| | | | |
|---|---|---|---|
| 6,070,099 A * | 5/2000 | Magin | 607/5 |
| 6,417,649 B1 | 7/2002 | Brink | |
| 6,737,847 B2 | 5/2004 | Watanabe et al. | |
| 6,871,090 B1 | 3/2005 | He et al. | |
| 7,127,288 B2 | 10/2006 | Sturman et al. | |
| 2003/0216786 A1* | 11/2003 | Russial | 607/5 |
| 2004/0116967 A1* | 6/2004 | DeGroot et al. | 607/5 |
| 2008/0154320 A1* | 6/2008 | Sherwood | 607/9 |

OTHER PUBLICATIONS

Borage et al: "Analysis and Design of an LCL-T Resonant Converter as a Constant-Current Power Supply"; IEEE Transactions on Industrial Electronics, vol. 52, No. 6, Dec. 2005, pp. 1547-1554.

Erickson et al: "Fundamentals of Power Electronics"; 2nd Edition, Kluwer, 2001, in Chapter 19, Figures 19.47 and 19.48.

Erickson et al: "Fundamentals of Power Electronics"; 2nd Edition, Kluwer 2001, in Chapter 12, Figure 12.1.

* cited by examiner

BIOMEDICAL ELECTRO-STIMULATOR

FIELD OF THE INVENTION

The invention relates to the field of biomedical electro-stimulators, more specifically to the field of electric circuits for driving such biomedical electro-stimulator.

BACKGROUND OF THE INVENTION

Biomedical electro-stimulators, such as cardiac pacemakers or neural stimulators, are often based on providing electric stimulation pulses to the human tissue with an electrode by discharge from a storage or holding capacitor in the electro-stimulator circuit. Between the stimulation discharges, this capacitor is charged from an energy source, e.g. a battery, to obtain the desired stimulation voltage for applying as a stimulation pulse to the tissue. Different strategies are used for charging the storage capacitor, thus affecting the energy efficiency of the electro-stimulator circuit. Energy efficiency is a crucial quality parameter especially for implanted battery-driven electro-stimulators such as pacemakers, since the implanted patient often needs a surgery in order to replace the battery. Lifetime of a given battery is directly influenced by the energy efficiency of the electro-stimulator circuit, which is in turn strongly determined by the amount of resistive losses.

An example of a charging circuit in a biomedical electro-stimulator can be found in U.S. Pat. No. 6,871,090. An inductive DC-DC converter (inductive boost converter), which can be modeled in steady state as a variable voltage source, charges a storage capacitor by converting energy from a battery. The charging capacitor is then charged to the voltage used for generating stimulation pulses. With such charging circuit it is possible to precisely control the charge voltage on the storage capacitor without the need for a power consuming linear voltage regulator.

SUMMARY OF THE INVENTION

According to the above explanation, it is an object to provide an energy efficient circuit for biomedical electro-stimulators in order to increase battery lifetime in biomedical electro-stimulator devices. Still, the circuit should preferably be rather simple such that it can be implemented also in miniature scale so as to suit also miniature electro-stimulators for implantation. Further, the charging voltage should preferably be precisely controllable without the need for a power consuming linear voltage regulator.

In a first aspect, the invention provides a biomedical electro-stimulator circuit arranged to generate a stimulation pulse to an associated electrode, based on energy stored in a storage capacitor, the circuit including a charging circuit arranged to control charging of the storage capacitor, also called a holding capacitor, based on electric energy from an associated energy source, the charging circuit including an energy converter arranged to apply a charging current to the storage capacitor, the charging current being substantially constant over a charging period.

By 'the charging current being substantially constant over a charging period' is understood that during the majority of the charging time, the current is kept constant or in practice almost constant, i.e. within a current variation of less than 30% from an average value over the charging period. Preferably, the variation is less than 20%, such as less than 10%. Hereby is understood that during the charging period, the current will always be within +/−30% of the average charging current, such as within +/−20% of the average charging current, such as within +/−10% of the average charging current. It is understood that a short charging start-up time where the charging current rises from zero to a predetermined substantially constant current value, is not included in what is denoted the 'charging period'. Such substantially constant charging current during the charging period is significantly different from prior art charging circuits, where the charging current start at an initial maximum current and then decreases exponentially until the desired voltage across the capacitor is reached, and thus the initial maximum charging current may be several times higher than the average charging current during the charging period.

By charging the storage capacitor with a constant current, the charging current can be kept rather low, and therefore resistive losses in various circuit elements in the charging signal path are minimized compared to other charging schemes. By applying a constant charging current, the voltage across the storage capacitor will increase approximately linearly over the charging period, until the desired voltage is reached.

The invention is based on the insight that for relevant values of: resistive losses, storage capacitor values, available charging periods (e.g. approximately 10 ms for neural stimulation), and charging voltages in biomedical electro-stimulators, the most energy efficient charging of the storage capacitor is a slow charging with a constant charging current during the available charging period. Thus, the same charging efficiency can not be obtained with the solution proposed e.g. in U.S. Pat. No. 6,871,090 as described, because the DC-DC converter used there behaves as a voltage source and cannot control the charging current to a substantially constant value. Charging a capacitor using a voltage source will provide a charging current that varies considerably during the charging period, i.e. a charging scheme which is not optimal with respect to power efficiency in biomedical electro-stimulation applications.

In preferred embodiments, the energy converter is an inductive energy converter, such as implemented by an inductive DC-DC converter circuit topology, most preferably an inductive DC-DC converter arranged to function as a current source. Especially, such inductive energy converter embodiment may include a control circuit arranged to measure a switch current of the energy converter circuit and to control the energy converter circuit accordingly, in order to provide the substantially constant charging current. Such control circuit may be arranged to control the energy converter circuit according to a predetermined maximum current value, and thus the control circuit may be arranged to receive an input allowing selection or adjustment of a desired charging current value.

The inductive energy converter circuit preferably includes an inductor, e.g. a copper coil, arranged to apply the substantially constant charging current to the storage capacitor.

In other embodiments, the energy converter includes an energy converter circuit based on conversion of energy via a resonator, such as a series connection of an inductor and a capacitor. The resonator may alternatively be a more complicated resonator circuit involving more components.

The energy converter may alternatively be a capacitive energy converter. Even though such capacitive energy converter may not have the same energy efficiency as an inductive energy converter, the capacitive energy converter is advantageous since it only requires a limited amount of space, and it may be more convenient to use in combination with Magnetic Resonance scanners due to a higher magnetic immunity.

The biomedical electro-stimulator circuit preferably includes a circuit arranged to form the stimulation pulse based on energy stored in the storage capacitor.

In a second aspect, the invention provides method for charging a storage capacitor in a biomedical electro-stimulator arranged for generating a stimulation pulse, the method including converting electric energy received from an energy source to a substantially constant charging current, and charging the storage capacitor with the substantially constant charging current during a charging period.

The method may be implemented in hardware, in software or in a combination of hardware and software.

In a third aspect, the invention provides a biomedical electro-stimulator device including a biomedical electro-stimulator circuit according to the first aspect, an energy source arranged for connection to the biomedical electro-stimulator circuit, and an electrode arranged for receiving the stimulation pulse generated by the biomedical electro-stimulator circuit.

Especially, the biomedical electro-stimulator device may include a casing for housing the biomedical electro-stimulator circuit and the energy source, the casing being arranged for medical implanting. Especially, the energy source may be an electric battery.

The biomedical electro-stimulator device may be any electric stimulation device for a therapeutic purpose. The biomedical electro-stimulator device may be one of: a cardiac pacemaker, a neural stimulator, a cochlear stimulator, a functional electric stimulation device, a muscle stimulator for prosthetic purposes.

It is appreciated that embodiments and advantages mentioned for the first aspect apply as well for the second and third aspects. Further, it is appreciated that the mentioned aspects and embodiments thereof may be combined in any way.

BRIEF DESCRIPTION OF THE DRAWINGS

Embodiments of the invention will be described, by way of example only, with reference to the drawings, in which.

DETAILED DESCRIPTION OF EMBODIMENTS

Figure 1:
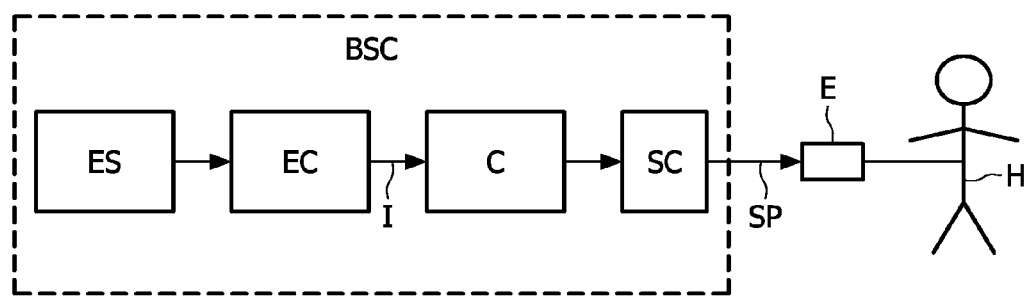
FIG. 1 illustrates a block diagram of a biomedical electro-stimulator embodiment.

FIG. 1 illustrates a biomedical electro-stimulator arranged to generate an electric stimulation of a part of a human body H, e.g. the heart, via an electrode E. The biomedical electro-stimulator circuit BSC provides a stimulation pulse SP to the electrode E that is in contact with the human tissue and thus applies an electric stimulation.

In the embodiment shown in FIG. 1, the biomedical electro-stimulator circuit BSC includes an energy source ES, e.g. a battery, that delivers electric energy to an energy converter EC. The energy converter EC converts the electric energy from the source ES to a charging current I which is applied to a storage capacitor C, so as to charge the storage capacitor C to a predetermined voltage. A stimulation pulse circuit SC then forms the stimulation pulse SP to be applied to the electrode E based on the energy stored in the storage capacitor C. In preferred embodiments, the energy converter includes an inductive energy converter arranged to provide a rather low and constant charging current for charging the storage capacitor C to the desired voltage, such as will be described in more details later.

Figure 2:
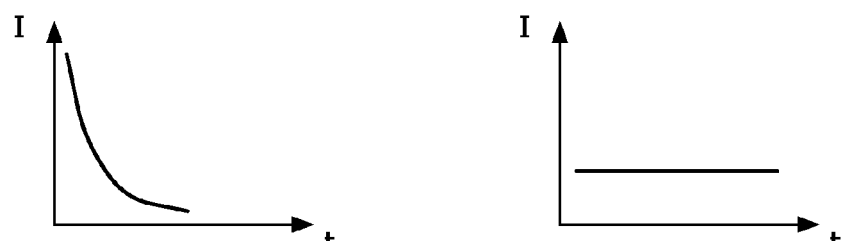
FIG. 2 illustrates charging current versus time for charging a storage capacitor of the biomedical electro-stimulator.

FIG. 2 shows two graphs illustrating charging current I versus time t during one charging period for charging of the storage capacitor C. The graph to the left indicates a typical charging scheme according to prior art, i.e. a current that varies significantly during the charging period, thus having a rather high peak current, thereby resulting in a rather high energy loss in resistive elements of the biomedical electro-stimulator circuit BSC.

In FIG. 2, the graph to the right indicates a constant charging current I versus time according to the invention. To the right, the current is seen to have a constant level throughout the charging period, thereby resulting in a low peak current level, meaning that energy loss in resistive elements in the biomedical electro-stimulator circuit BSC is kept to a minimum. Compared to the graph of the prior art charging shown to the left, the charging period (shown with double arrows) according to the invention will be longer, since preferably the available time between stimulation pulses is utilized for the charging choosing the lowest possible charging current, thereby providing the most energy efficient charging.

Figure 3A:
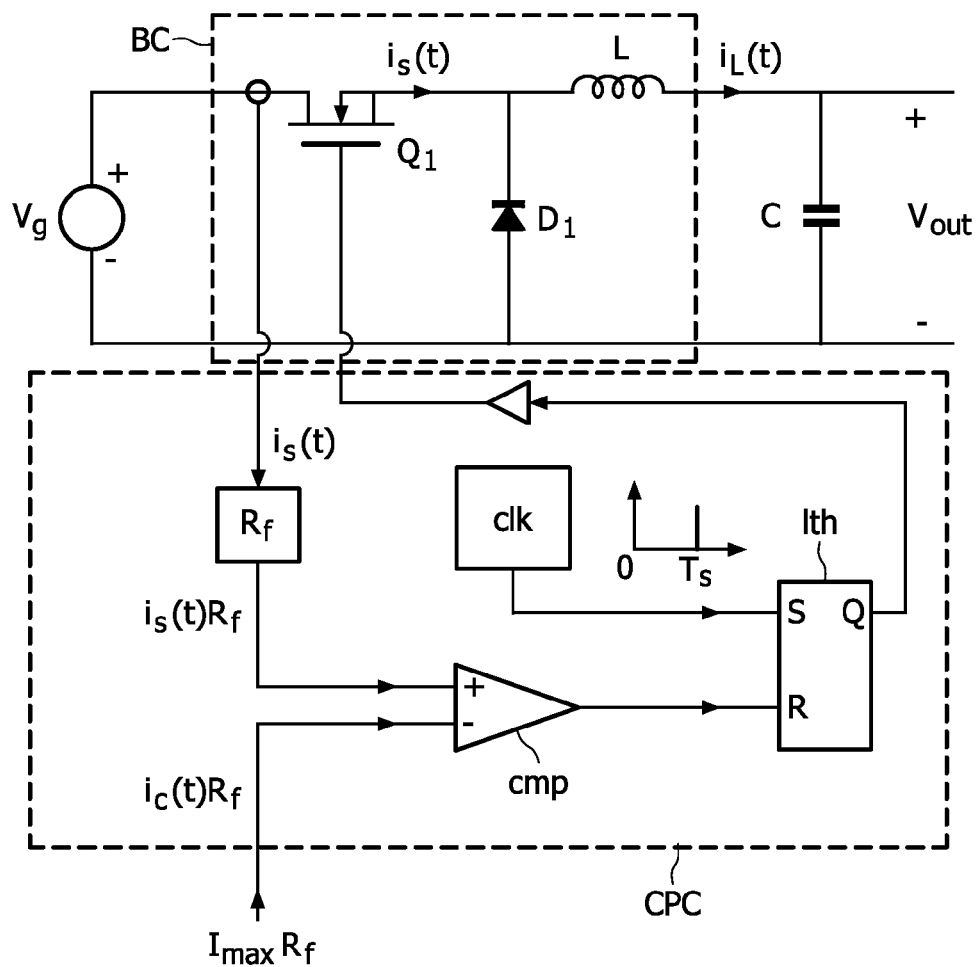
FIG. 3a illustrates a circuit diagram of one circuit embodiment.
Figure 3B:
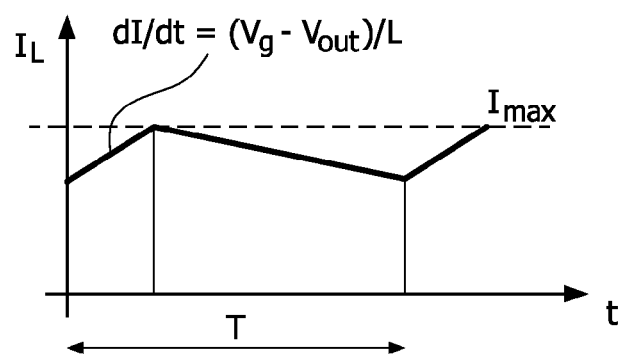
FIG. 3b illustrates charging current during a charging period for the embodiment of FIG. 3a, and FIG. 4 illustrates a circuit diagram of another circuit embodiment.

FIG. 3a illustrates one embodiment of a biomedical electro-stimulator circuit, or at least the charging part of such circuit. An inductive buck DC-DC converter BC is used to charge the storage capacitor C to a voltage Vout by converting electric energy from the voltage source Vg, e.g. a battery. Current $i_s(t)$ flowing through the switch Q1, e.g. a transistor, is measured by a control circuit in the form of a current programmed controller CPC that includes a control loop comparing the measured current $i_s(t)$ to a predetermined set point, $I_{max}R_f$. When the current $i_s(t)$ in the switch exceeds this predetermined maximum current, the switch Q1 is opened. With such arrangement, the maximum current charging the capacitor C can be set, and excessive current peaks during the charging up of the capacitor C can be avoided, together with excessive energy losses due to the series resistance of the devices in which the charging current flows (i.e. the inductor L, the switch Q1 and the rectifier D1).

In the illustrated embodiment of the current programmed controller CPC, an analog comparator cmp is connected to compare a measure of the current $R_f i_s(t)$ and a measure of a reference max current $R_f i_s(t)$. Output of the comparator cmp is connected to the switch Q1 via a latch lth, the latch lth being connected also to a clock generator clk. Further details in relation to the circuit shown in FIG. 3a may be found in FIG. 12.1 and description thereof in "Fundamentals of power electronics", R. Erickson and D. Maksimovic, 2nd Edition, Kluwer 2001.

To further optimize the embodiment of FIG. 3a, the following two items may be considered:

1) The rate of variation di/dt of the current flowing through transistor Q1 can be easily calculated on the bases of the value of the inductor L, and the difference between the source voltage $V_g$ and the capacitor voltage $V_{out}$. For a difference $V_g-V_{out}$ of 1V and an inductance of 1 mH (which is a quite large value), the di/dt is in the order of 103 A/s. Thus, in case the peak current should be controlled to an accuracy of e.g. 10 μA, the control loop of the current programmed controller CPC has to switch off the transistor Q1 within 10 ns, which is possible but requires a considerable amount of power to be used in the control loop.

2) The operation of the switches in a buck (or boost) converter can be made more energy efficient using zero voltage switching for Q1 and substituting the diode D1 with a synchronous rectifier. To obtain zero-voltage switching in this kind of topology, the converter must be working in "Discontinuous Conduction Mode" (DCM). In other words, the inductor current $i_s(t)$ must be allowed to become negative, and the ratio between peak inductor current and mean current flowing in the output capacitance will become large, resulting in a trade-off between a better efficiency in operating the switches and a larger resistive loss in the parasitic resistances present in the circuit.

Figure 4:
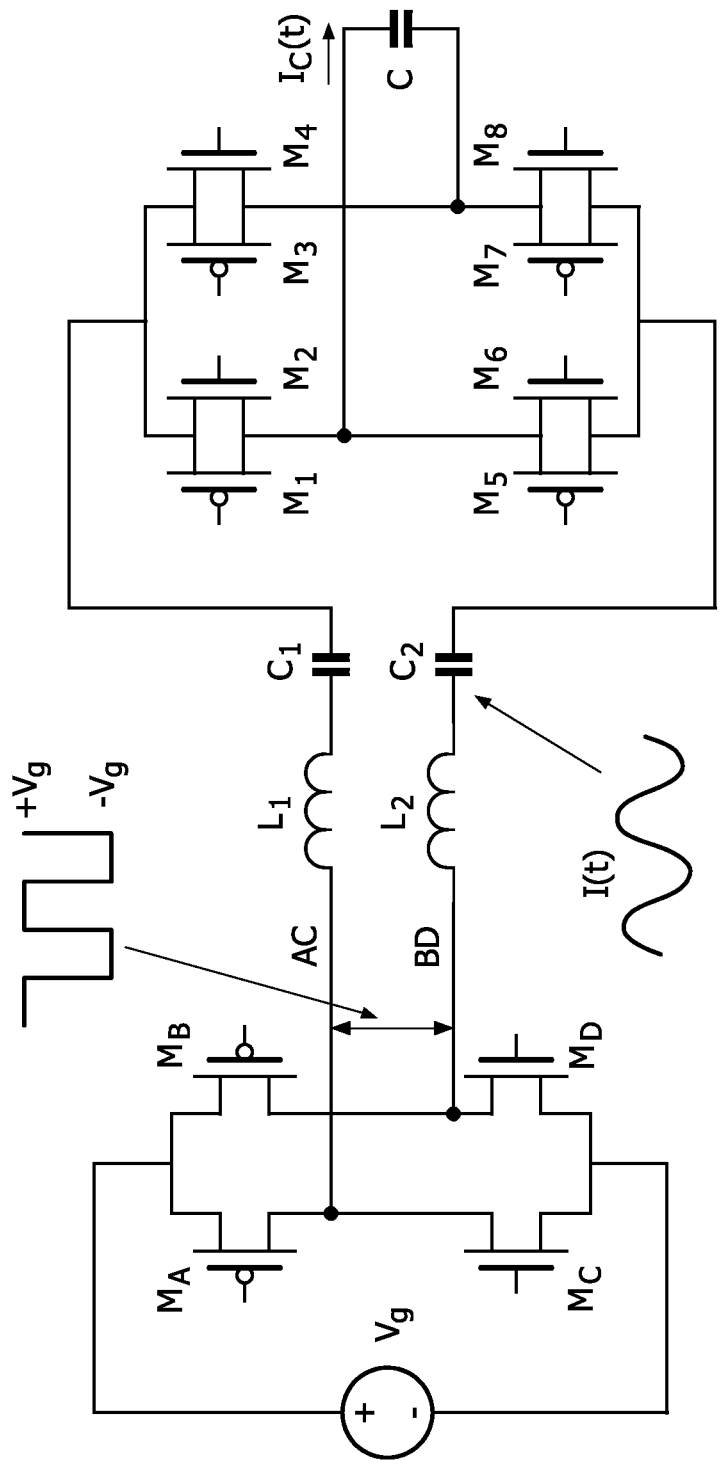

FIG. 4 illustrates a circuit diagram of another embodiment. In this circuit the energy converter is based on a series-resonant DC-DC converter, which charges the storage capacitor C based on energy from the energy source Vg. The converter comprises a full bridge including switches MA, MB, MC and MD that serve to switch the voltage from the energy source Vg so as to provide a square wave voltage between AB and BD, such as illustrated. The series resonator includes two respective set of series connected inductor and capacitor L1, C1 and L2, C2, via which the switched voltage from nodes AB and BD are applied to a synchronous, full wave rectifier implemented with 8 transistors M1-M8, that finally is connected to the storage capacitor C, delivering a charging current $I_C(t)$.

Output characteristics of such series resonant converter can be seen e.g. in the book "Fundamentals of power electronics", by R. Erickson and D. Maksimovic, 2nd Edition, Kluwer, 2001, in FIGS. 47 and 48 of Chapter 19. For switching frequencies above resonance, i.e. for frequencies higher than 1.3 times the resonance frequency, the converter has approximately the behavior of a current source. For frequencies below half the resonance frequency, the converter has an exact current-source output characteristic. Thus, the circuit shown in FIG. 4, operated at the correct switching frequency, will intrinsically provide a constant current charging of the storage capacitor C, and an efficient conversion of energy from the energy source Vg to the storage capacitor C, at least from the viewpoint of the resistive losses.

The circuit of FIG. 4 does not need any specific control circuit during normal operation of the converter. However, a control circuit may be included, such control circuit including a (slow) comparator that switches off the converter when the voltage across the capacitor C has reached the required voltage level, and switches it on again when the capacitor C must be recharged, to start another charging cycle.

It may be seen as a drawback of the circuit illustrated in FIG. 4, that quite many switches are used, thereby increasing the series resistance seen by the current flowing in the resonant circuit and the capacitive switching losses. However, this drawback is mitigated by the fact that when the power switches MA-MD of the full bridge are switched at a frequency above resonance, they will see an inductive load provided by the series resonator above resonance. This allows the designer to implement easily zero voltage switch-on and switch off, which enables more energy efficient switching. The pass gates of the synchronous full-wave rectifier, implemented with transistors M1-M8, can easily be operated in zero-current switching.

The waveform of the current I(t) flowing through the series resonator L1, C1 and L2, C2 in FIG. 4 is approximately sinusoidal, as illustrated also in FIG. 4, and has thus a defined peak-to-mean value ratio which is rather small (ideally the square root of 2). This helps, as already explained, keeping the energy losses in the resistive elements small.

It is to be understood, that many other implementations of energy converters that intrinsically provide a constant charging current are possible. As an additional example, a converter topology may be based on a LCL-T resonant, such as described in "Analysis and Design of an LCL-T Resonant Converter as a Constant-Current Power Supply" by Mangesh Borage, et al., IEEE Trans. on Industrial Electronics, Vol. 52, No. 6, December 2005.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

To sum up: a power efficient biomedical electro-stimulator circuit BSC is provided. The circuit BSC includes a charging circuit arranged to control charging of a storage capacitor C based on electric energy from an energy source ES, e.g. a battery. The charging circuit includes an energy converter EC that applies a charging current I to the storage capacitor C, this charging current I being substantially constant over a charging period T, thereby providing a power efficient charging. In preferred embodiments, the energy converter EC is an inductive energy converter, e.g. a DC-DC converter, with a control circuit serving to provide an almost constant charging current during the charging period. In another embodiment, the energy converter EC is an energy converter that charges the storage capacitor via a series resonator, e.g. a series connection of an inductor and a capacitor. The proposed biomedical electro-stimulator circuit is advantageous for devices such as pacemakers, and neural stimulation etc. which can benefit of increased battery lifetime due to an efficient charging scheme.

Reference signs are included in the claims, however the inclusion of the reference signs is only for clarity reasons and should not be construed as limiting the scope of the claims.

The invention claimed is:

1. A biomedical electro-stimulator circuit arranged to generate a stimulation pulse to an associated electrode, the circuit comprising:
   a storage capacitor configured to generate the simulation pulse;
   an energy source configured to charge the storage capacitor;
   a full-wave rectifier circuit arranged to control charging of the storage capacitor based on electric energy from the energy source and to apply a charging current to the storage capacitor, the charging current being substantially constant over a charging period; and
   an inductor coupled in series between the energy source and the rectifier circuit, wherein the electrical energy is received by the rectifier circuit through the inductor.

2. The circuit according to claim 1, comprising a control conduit arranged to measure a voltage across the capacitor to stop supplying the charging current when the voltage exceeds a predetermined voltage level.

3. The circuit according to claim 1, wherein the rectifier circuit is arranged to receive a varying current from the inductor to apply the substantially constant charging current to the storage capacitor.

4. The circuit according to claim 1, wherein inductor is arranged as a resonator operating as an energy converter circuit based on conversion of energy via the resonator.

5. The circuit according to claim 4, wherein the resonator includes a series connection of the inductor and a capacitor.

6. The circuit according to claim 1, wherein the rectifier circuit is arranged to apply a charging current, that varies less than 10%, over the charging period.

7. A method for charging a storage capacitor in a biomedical electro-stimulator arranged for generating a stimulation pulse, the method comprising acts of:
coupling an inductor between an energy source and a full-wave rectifier circuit;
converting by the rectifier circuit, electric energy received from the energy source through the inductor to a substantially constant charging current, and
charging the storage capacitor with the substantially constant charging current during a charging period.

8. A biomedical electro-stimulator device comprising:
a biomedical electro-stimulator circuit;
an energy source arranged for connection to the biomedical electro-stimulator circuit;
a storage capacitor; and
an electrode arranged for receiving a stimulation pulse generated by the biomedical electro-stimulator circuit, wherein the biomedical electro-stimulator circuit includes a full-wave rectifier circuit arranged to apply a charging current to the storage capacitor, the charging current being substantially constant over a charging period, and an inductor coupled in series between the energy source and the rectifier circuit, where the rectifier circuit receives electrical energy from the energy source through the inductor.

9. The biomedical electro-stimulator device according to claim 8, comprising a casing for housing the biomedical electro-stimulator circuit and the energy source, the casing being arranged for medical implanting.

10. The biomedical electro-stimulator device according to claim 8, being one of: a cardiac pacemaker, a neural stimulator, a cochlear stimulator, a functional electric stimulation device, and a muscle stimulator for prosthetic purposes.

* * * * *